(12) United States Patent
Beulke et al.

(10) Patent No.: US 7,740,644 B2
(45) Date of Patent: Jun. 22, 2010

(54) EMBOLIC PROTECTION FILTERING DEVICE THAT CAN BE ADAPTED TO BE ADVANCED OVER A GUIDEWIRE

(75) Inventors: Mel R. Beulke, Bloomington, MN (US); Anthony C. Vrba, Maple Grove, MN (US); Brian J. Lowe, Zimmerman, MN (US); Thomas E. Broome, Shakopee, MN (US); Dennis A. Boismier, Shorewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 839 days.

(21) Appl. No.: 10/373,137

(22) Filed: Feb. 24, 2003

(65) Prior Publication Data

US 2004/0167565 A1   Aug. 26, 2004

(51) Int. Cl.
*A61M 29/00* (2006.01)
(52) U.S. Cl. .................................... 606/200
(58) Field of Classification Search ........... 606/200, 606/194, 108, 159; 604/103.04, 104–107
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,494,531 A | 1/1985 | Gianturco | |
| 4,590,938 A | 5/1986 | Segura et al. | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,873,978 A | 10/1989 | Ginsburg | |
| 4,921,478 A | 5/1990 | Solano et al. | |
| 4,921,484 A | 5/1990 | Hillstead | |
| 4,926,858 A | 5/1990 | Giffort, III et al. | |
| 4,969,891 A | 11/1990 | Gewertz | |
| 4,998,539 A | 3/1991 | Delsanti | |
| 5,002,560 A | 3/1991 | Machold et al. | |
| 5,011,488 A | 4/1991 | Ginsburg | |
| 5,053,008 A | 10/1991 | Bajaj | |
| 5,071,407 A | 12/1991 | Termin et al. | |
| 5,100,423 A | 3/1992 | Fearnot | |
| 5,102,415 A | 4/1992 | Guenther et al. | |

(Continued)

FOREIGN PATENT DOCUMENTS

DE   28 21 048   7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner*—Anhtuan T Nguyen
*Assistant Examiner*—Elizabeth Houston
(74) *Attorney, Agent, or Firm*—Crompton, Seager & Tufte LLC

(57) ABSTRACT

An improved embolic protection filtering device. In at least some embodiments, an embolic protection filtering device includes a filter wire assembly. The filter wire assembly may include an elongate shaft, a tubular member, and an embolic protection filter.

38 Claims, 11 Drawing Sheets

U.S. PATENT DOCUMENTS

| | | | |
|---|---|---|---|
| 5,133,733 A | 7/1992 | Rasmussen et al. | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,224,953 A | 7/1993 | Morgentaler | |
| 5,324,303 A | 6/1994 | Strong et al. | |
| 5,329,942 A | 7/1994 | Gunther et al. | |
| 5,330,484 A | 7/1994 | Gunther | |
| 5,354,310 A | 10/1994 | Garnie et al. | |
| 5,370,657 A | 12/1994 | Irie | |
| 5,376,100 A | 12/1994 | Lefebvre | |
| 5,383,887 A | 1/1995 | Nadal | |
| 5,421,832 A | 6/1995 | Lefebvre | |
| 5,423,742 A | 6/1995 | Theron | |
| 5,449,372 A | 9/1995 | Schmaltz et al. | |
| 4,842,579 A | 10/1995 | Shiber | |
| 5,456,667 A * | 10/1995 | Ham et al. | 604/107 |
| 5,462,529 A | 10/1995 | Simpson et al. | |
| 5,536,242 A | 7/1996 | Willard et al. | |
| 5,549,626 A | 8/1996 | Miller et al. | |
| 5,601,595 A | 2/1997 | Smith | |
| 5,626,605 A | 5/1997 | Irie et al. | |
| 5,634,942 A | 6/1997 | Chevillon et al. | |
| 5,649,953 A | 7/1997 | Lefebvre | |
| 5,658,296 A | 8/1997 | Bates et al. | |
| 5,662,671 A | 9/1997 | Barbut et al. | |
| 5,695,519 A | 12/1997 | Summers et al. | |
| 5,720,764 A | 2/1998 | Naderlinger | |
| 5,725,550 A | 3/1998 | Nadal | |
| 5,728,066 A | 3/1998 | Daneshvar | |
| 5,746,767 A | 5/1998 | Smith | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Bouewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,848,964 A | 12/1998 | Samuels | |
| 5,876,367 A | 3/1999 | Kaganov et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A * | 5/2000 | Engelson et al. | 606/200 |
| 6,068,645 A | 5/2000 | Tu | |
| 6,086,605 A | 7/2000 | Barbut et al. | |
| 6,117,154 A | 9/2000 | Barbut et al. | |
| 6,129,739 A | 10/2000 | Khosravi | |
| 6,136,016 A | 10/2000 | Barbut et al. | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,012 B1 | 6/2001 | Kleshinski | |
| 6,245,087 B1 | 6/2001 | Addis | |
| 6,245,088 B1 | 6/2001 | Lowery | |
| 6,245,089 B1 | 6/2001 | Daniel et al. | |
| 6,246,672 B1 | 6/2001 | Lumelsky | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,391,044 B1 * | 5/2002 | Yadav et al. | 606/200 |
| 6,398,756 B2 | 6/2002 | Peterson et al. | |
| 6,475,187 B1 * | 11/2002 | Gerberding | 604/102.02 |
| 6,506,203 B1 | 1/2003 | Boyle et al. | |
| 6,537,294 B1 * | 3/2003 | Boyle et al. | 606/200 |
| 6,692,513 B2 * | 2/2004 | Streeter et al. | 606/200 |
| 6,702,781 B1 * | 3/2004 | Reifart et al. | 604/96.01 |
| 6,818,006 B2 * | 11/2004 | Douk et al. | 606/200 |
| 2002/0022858 A1 * | 2/2002 | Demond et al. | 606/200 |
| 2003/0078614 A1 * | 4/2003 | Salahieh et al. | 606/200 |
| 2003/0093106 A1 * | 5/2003 | Brady et al. | 606/194 |
| 2003/0093110 A1 * | 5/2003 | Vale | 606/200 |
| 2004/0122466 A1 * | 6/2004 | Bales | 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |

| | | |
|---|---|---|
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Rediology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).
Cragg, Andrew et al., "Nonsurgical Placement of Arterial Endoprosthesis: A New Technique Using Nitinol Wire," AJR, pp. 261-263 (Apr. 1983).
Diethrich et al., "Percutaneous Techniques for Endoluminal Carotid Interventions," *J. Endovasc. Surg.*, 3:182-202 (1996).
Fadali, A. Moneim, "A filtering device for the prevention of particulate embolization during the course of cardiac surgery," Surgery, 64(3):634-639 (Sep. 1968).
Haissaguerre et al., "Spontaneous Initiation of Atrial Fibrillation by Ectopic Beats Originating in the Pulmonary Veins," *The New England Journal of Medicine*, 339(10):659-666 (Sep. 1988).
Jordan, Jr. et al., "Microemboli Detected by Transcranial Doppler Monitoring . . . ," Cardiovascular Surgery, 7(1)33-38 (Jan. 1999).
Lesh, "Can Catheter Ablation Cure Atrial Fibrillation?" *ACC Current Journal Review*, pp. 38-40 (Sep./Oct. 1997).
Lund et al., "Long-Term Patentcy of Ductus Arteriosus After Balloon Dilation: an Experimental Study," Laboratory Investigation, 69(4):772-774 (Apr. 1984).
Marache et al., "Percutaneous Transluminal Venous Angioplasty . . . ," *American Heart Journal*, 125(2 Pt 1):362-366 (Feb. 1993).
Mazur et al., "Directional Atherectomy with the Omnicath™: A Unique New Catheter System," Catheterization and Cardiovascular Diagnosis, 31:17-84 (1994).
Moussa, MD, Issaam "Stents Don't Require Systemic Anticoagulation . . . But the Technique (and Results) Must be Optimal," Journal of Invasive Cardiol., 8(E):3E-7E, (1996).
Nakanishi et al., "Catheter Intervention to Venous System Using Expandable Metallic Stents," Rinsho Kyobu Geka, 14(2):English Abstract Only (Apr. 1994).
Onal et al., "Primary Stenting for Complex Atherosclerotic Plaques in Aortic and Iliac Stenoses," Cardiovascular & Interventional Radiology, 21(5):386-392 (1998).
Tunick et al., "Protruding atherosclerotic plaque in the aortic archo f patients with systemic embolization: A new finding seen by transesophageal echocardiography," American Heart Journal 120(3):658-660 (Sep. 1990).
Waksman et al., "Distal Embolization is Common After Directional Atherectomy . . . ," *American Heart Journal*, 129(3):430-435 (1995).
Wholey, Mark H. et al., PTA and Stents in the Treatment of Extracranial Circulation, *The Journal of Invasive Cardiology*, 8(E):25E-30E (1996).

* cited by examiner

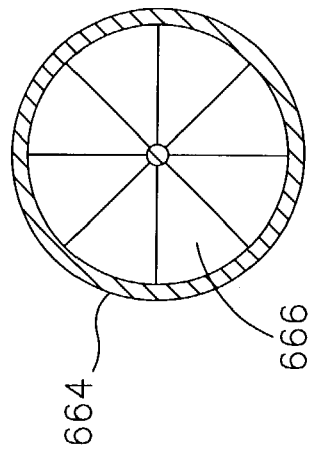
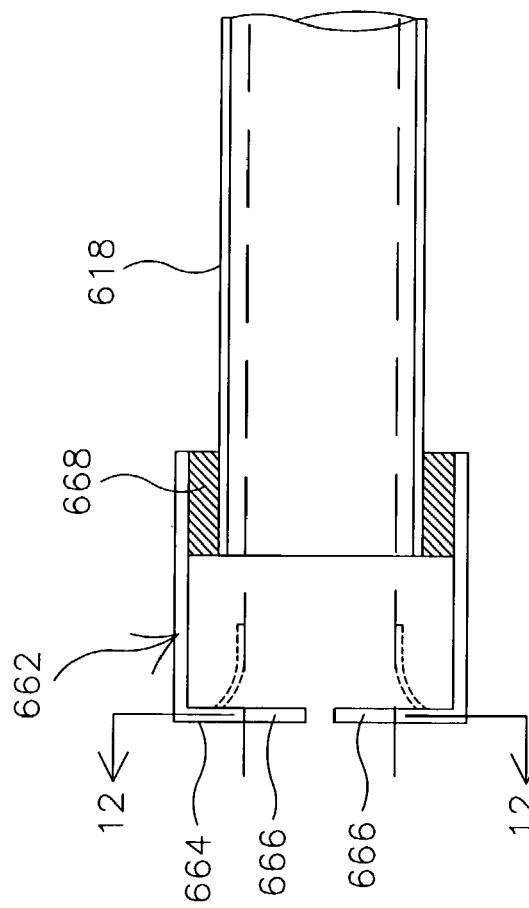
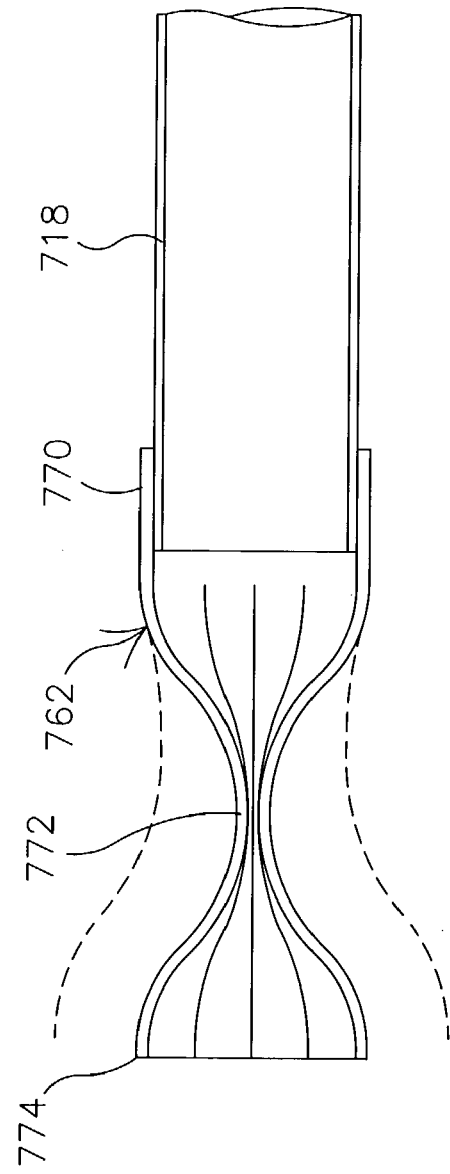

EMBOLIC PROTECTION FILTERING DEVICE THAT CAN BE ADAPTED TO BE ADVANCED OVER A GUIDEWIRE

FIELD OF THE INVENTION

The present invention pertains to embolic protection devices. More particularly, the present invention pertains to embolic protection devices that can be advanced over a medical device such as a guidewire.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

BRIEF SUMMARY

The present invention pertains to embolic protection filtering devices. In some embodiments, a filtering device includes a filter wire assembly having an embolic protection filter coupled thereto. The filter wire assembly may include a filter wire and a tubular member having a lumen that is configured for having a shaft or guidewire disposed therein. According to this embodiment, the filtering device can be adapted for being delivered over essentially any guidewire or any other appropriate medical device.

The filtering device may also include a delivery and/or retrieval sheath. The sheath may include a lumen for receiving the filter wire and a lumen for receiving the guidewire. Thus, the sheath can be used to deliver the filtering device by disposing the filter at least partially therein and advancing the sheath over a guidewire. Similarly, the sheath may be used to retrieve the filter by advancing it over the guidewire to a location adjacent the filter so that the filter becomes at least partially disposed therein. Further features and description of these and other embodiments of the invention are described in more detail below.

BRIEF DESCRIPTION OF THE DRAWINGS

FIG. 11 is a partial cross-sectional side view of another example flow blocking member suitable for use with an embolic protection filtering system;

FIG. 12 is a cross-sectional view taken through line 12-12 of the flow blocking member shown in FIG. 11;

FIG. 13 is a partial cross-sectional side view of another example flow blocking member suitable for use with an embolic protection filtering system;

DETAILED DESCRIPTION

Figure 1:
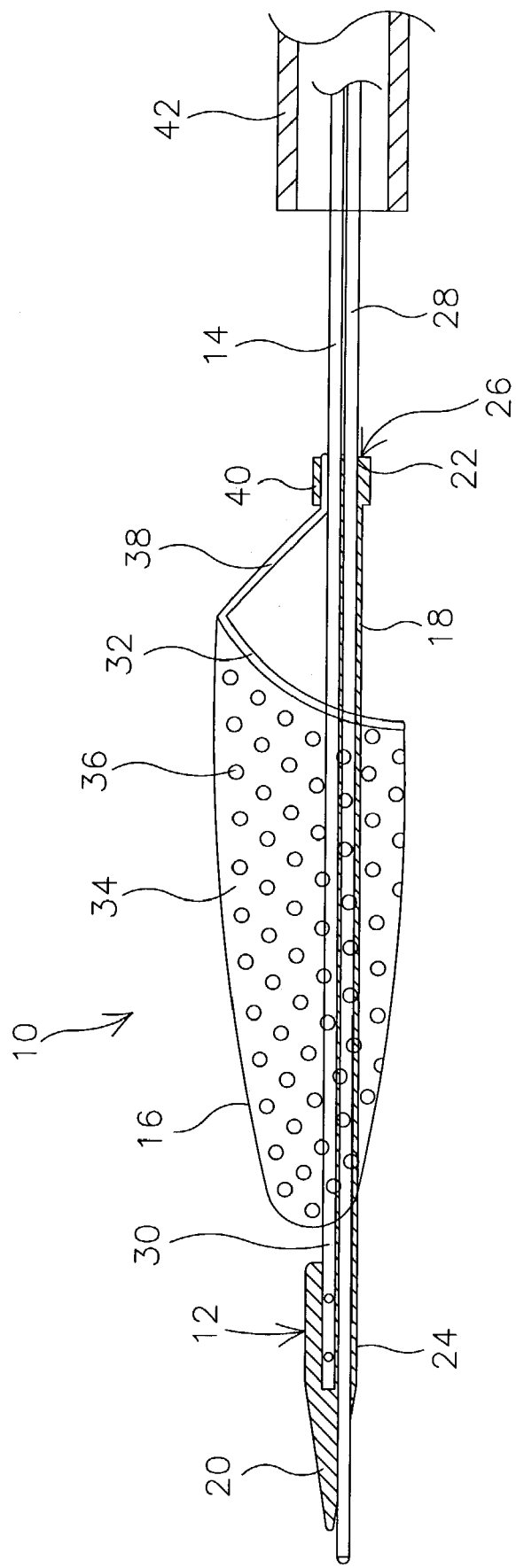
FIG. 1 is a partial cross-sectional view of an example embolic protection filter system.

The following description should be read with reference to the drawings wherein like reference numerals indicate like elements throughout the several views. The detailed description and drawings illustrate example embodiments of the claimed invention.

Intravascular interventions such as angioplasty, atherectomy, and the like, usually include the step of advancing a guidewire through the vasculature to a position adjacent an area of interest. Once the guidewire is positioned, a catheter (or other suitable medical device) can be advanced over the guidewire to the appropriate location. In the course of using a diagnostic or therapeutic catheter, embolic debris may dislodge from the blood vessel that can travel in the bloodstream and impair blood flow, possibly leading to tissue damage. To help reduce the chances of damage, a number of intravascular filtering devices have been developed that can be disposed in the blood vessel downstream of the target site and expanded to capture debris. Often these filtering devices are attached to a guidewire.

Because the exact state of intravascular lesion may not be fully known at the outset of the intervention, treating or diagnosing an intravascular lesion often includes repeated advancing and retracting of various medical devices. For example, an intervention that may be initiated as a diagnostic procedure may ultimately necessitate an immediate secondary intervention. In these situations, the already placed guidewire may not include a filtering device. The nature of the new procedure may make it desirable to replace the guidewire with one that includes a filtering device. In order to do so, the first guidewire (without a filter) can be removed and then a second guidewire (with a filter attached) can then be advanced to the appropriate location. These repeated exchange steps can reduce the efficiency of the overall intervention and may increase the costs associated with the intervention. The present invention pertains to improvements to both embolic protection filter assemblies and to methods of using them. In at least some embodiments, the present invention includes an embolic protection filter device that can be advanced over a guidewire or other suitable medical device to an appropriate location. The device, for example, can help improve the efficiency of intravascular interventions, help to control the costs associated with the intervention, allow a clinician to use a filtering device with an already-placed guidewire when filtering is desired, help reduce the profile of the filtering device and/or associated delivery and retrieval catheters, as well as impart a number of additional desirable features and benefits as described in more detail below.

FIG. 1 is a partial cross-sectional view of an example embolic protection filter device 10. Device 10 may include a filter wire assembly 12. The filter wire assembly may include an elongate shaft or filter wire 14 and an embolic protection filter 16 disposed, for example, adjacent filter wire 14. Filter wire assembly 12 may also include a tubular member 18 and a distal nosecone 20. Tubular member 18 may include a proximal end 22, a distal end 24, and a lumen 26 extending between the proximal and distal ends 22/24.

In at least some embodiments, lumen 26 may comprise a guidewire lumen that has an inside diameter that is adapted and configured for having a guidewire 28 slidably disposed therein. This structural feature allows device 10 to be advanced over essentially any "off-the-shelf" guidewire 28 to an appropriate intravascular location in order to filter embolic debris. For example, the inside diameter of lumen 26 may be configured for having guidewire 28 with an outside diameter in the range of about 0.008 to about 0.020 inches or more to be slidably disposed therein. It can be appreciated, however, that alternative embodiments of the invention include device 10 with lumen 26 having an inside diameter that is sized to be used with essentially any suitable medical device. For example, lumen 26 may be configured for use with a catheter, an endoscopic device, a laproscopic device, guidewires that are "atypical" or otherwise have an outside diameter outside the abovementioned range, and the like.

The general configuration of tubular member 18 may include openings or ports that can be disposed at differing locations. For example, FIG. 1 depicts tubular member as having openings adjacent proximal and distal ends 22/24. It can be appreciated, however, that the precise locations of these openings can be varied without departing from the spirit of the invention. Additionally, the length or arrangement of tubular member 18 can also be altered. For example, it may be desirable for proximal and distal ends 22/24 to be disposed on opposite ends of filter 16 as shown in FIG. 1. Alternatively, proximal and/or distal ends 22/24 can be positioned at different locations. For example, proximal end 22 may be disposed distally of coupling 40 (but proximally of filter frame 32), distally of filter frame 32, distally of filter 16, or any other suitable location.

In at least some embodiments, filter wire assembly 12 is a singular structure (such as a tube or partially tubular shaft). According to these embodiments, tubular member 18 can be comprised of the same material as distal nosecone 20 or, in examples where filter wire assembly 12 is comprised of a mixture or composite of materials, tubular member 18 may be comprised of a different material than distal nosecone 20. For example, filter wire assembly 12 may be comprised of a metal-polymer composite that metallic materials adjacent tubular member 18 and relatively flexible polymeric materials adjacent distal nosecone 20. It can be appreciated that variations in the composition of filter wire 12 can be made without departing from the spirit of the invention.

Alternatively, tubular member 18 and distal nosecone 20 may comprise a plurality of structural elements that are attached or otherwise coupled to one another to define filter wire assembly 12. For example, tubular member 18 may comprise a generally tubular shaft or shaft having lumen 26 as described above and distal nosecone 20 may comprise an atraumatic, polymeric nosecone. These distinct structures can be attached by a number of different methods. For example, tubular member 18 and distal nosecone 20 may be attached by adhesives, brazing, welding, mechanical bonding, thermal bonding, and the like.

Suitable materials for the components of filter wire assembly 12 (in any of the above-mentioned arrangements or embodiments) include metals, polymers, metal-polymer composites, or any other appropriate material. Some examples of suitable metals and metal alloys include stainless steel, such as 304 v stainless steel; nickel-titanium alloys such as super elastic or linear elastic nitinol, nickel-chromium alloy, nickel-chromium-iron alloy, cobalt alloy, or the like; or other suitable material. Some examples of suitable polymers include polyurethane, polyether-ester (for example a polyether-ester elastomer such as ARNITEL® available from DSM Engineering Plastics), polyester (for example a polyester elastomer such as HYTREL® available from DuPont), or linear low density polyethylene (for example REXELL®), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene, Marlex high-density polyethylene, polyetheretherketone (PEEK), polyimide (PI), and polyetherimide (PEI), a liquid crystal polymer (LCP) alone or blended with other materials, and the like, or mixtures, combinations, or copolymers thereof.

Moreover, filter wire assembly 12 (or essentially any other appropriate structure described herein) may include a structure or combination of structures that are comprised of, coated with, or otherwise coupled to a radiopaque material. Radiopaque materials are understood to generally produce a relatively bright image on a fluoroscopy screen during a medical procedure. This relatively bright image aids the user of device 10 in determining its location. Radiopaque materials can include, but are not limited to, bismuth subcarbonate, iodine, gold, platinum, palladium, tantalum, tungsten or tungsten alloy, and the like. Some examples of suitable structures for used with assembly 12 include a marker band of radiopaque material, a radiopaque coil, a polymeric material doped with a radiopaque material, and the like.

Filter wire 14 may be comprised of an elongate shaft coupled to filter wire assembly 12. It is generally understood that filter wire 14 includes a proximal end (not shown) that can be made accessible to the clinician and can be used to advance filtering device 10 over guidewire 28 in a manner known in the art. In some embodiments, filter wire 14 has a structure that is similar to typical intravascular guidewire except that the portion is attached to filter wire assembly 12, for example adjacent distal nosecone 20. Alternatively, a portion of filter wire 14 can extend distally beyond the distal nosecone 20 and may include a spring or otherwise atraumatic tip. In some embodiments, filter wire 14 may integral with or otherwise comprise an extension of or a component of filter wire assembly 12. According to this embodiment, it would be appropriate to designate the combination of filter wire 14 and filter wire assembly 12 as a singular structural element (e.g., a shaft or shaft assembly) having above-mentioned components.

Filter 16 is generally adapted to operate between a first generally collapsed configuration and a second generally expanded configuration for collecting debris in a body lumen. Filter 16 may include a filter mouth or frame 32 having a filter material 34 coupled thereto. Frame 32 may be comprised of a "self-expanding" shape-memory material such as nickel-titanium alloy (to bias filter 16 to be in the second expanded configuration). Additionally, frame 32 may include a radiopaque material or include, for example, a radiopaque wire disposed about a portion thereof. Filter material 34 can be drilled (for example, formed by known laser techniques) or otherwise manufactured to include at least one opening 36. The holes or openings 36 are sized to allow blood flow therethrough but restrict flow of debris or emboli floating in the body lumen or cavity. One or more struts 38 may extend between frame 32 and filter wire 14 (and/or filter wire assembly 12) and be coupled to filter wire 14 and/or assembly 12 by a coupling 40. Coupling 40 may be one or more windings of struts 38 about filter wire 14 and/or assembly 12 or be a fitting disposed over an end of struts 38 to attach it to filter wire 14. At the distal end and/or along the length of filter 16, filter 16 may be attached or sealed to tubular member 18 by an appropriate sealer, for example epoxy.

To aid in the delivery or retrieval of filter 14 to an appropriate location, device 10 may also include a delivery or retrieval sheath 42. Device 10, according to this embodiment, may be configured so that filter 14 can be collapsed within sheath 42 and advanced over guidewire 28 to the desired location. Once device 10 is positioned at the desired location, sheath 42 can be retracted proximally to allow filter 14 to expand. Additionally, sheath 42 (or another appropriate retrieval device) can be re-advanced over guidewire 14 toward device 10 so that filter 14 can be collapsed and disposed within sheath 42. Once properly configured, sheath 42 and device 10 can be removed from the blood vessel.

Figure 2:
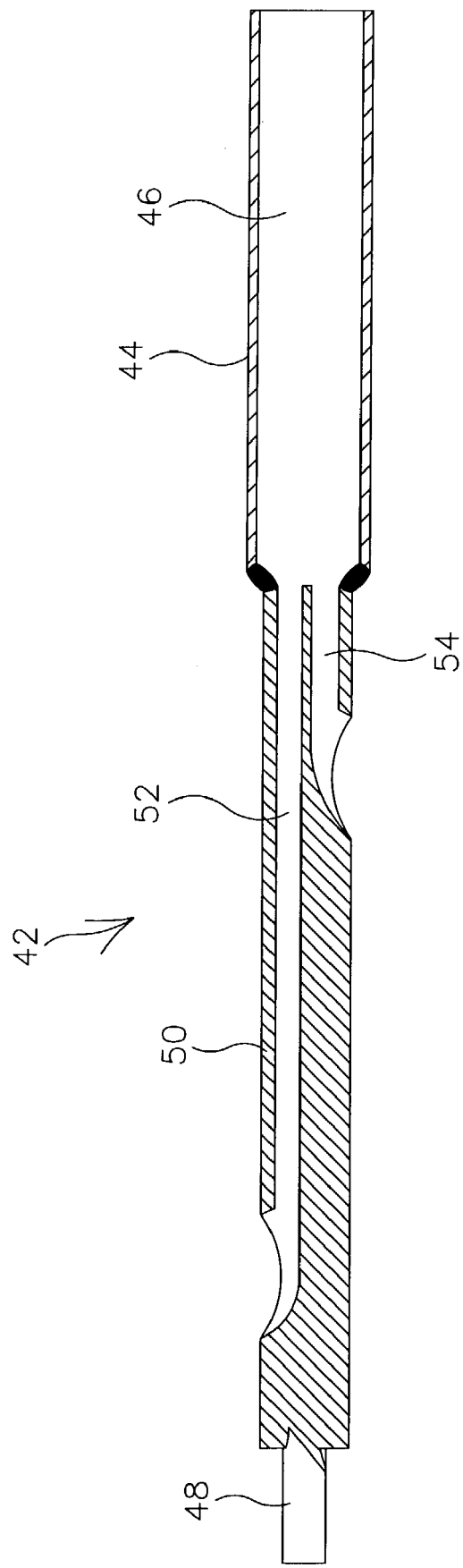
FIG. 2 is a partial cross-sectional view of an example embolic protection delivery and/or retrieval sheath.

One example embodiment of sheath 42 is shown in FIG. 2. Sheath 42 may include a distal region 44 having a filter chamber 46, a support member 48, and a mid-region 50 that can include a first lumen 52 and a second lumen 54. In at least some embodiments, sheath 42 may be adapted and configured to deliver and/or retrieve assembly 10 to and/or from an appropriate location. For example, device 10 can be delivered using sheath 42 by disposing filter 16 at least partially within filter chamber 46 (which may result in partial or complete collapsing of filter 16 within chamber 46) and by disposing filter wire 14 within lumen 52. Device 10 and sheath 42 can then be advanced over guidewire 28 (by disposing guidewire 28 in lumen 54) through the vasculature to an appropriate location. When properly positioned, sheath 42 can be retracted relative to device 10 and guidewire 28, thereby allowing filter 16 to be delivered from chamber 46 and expand within the vessel.

Alternatively, sheath 42 may be used to retrieve device 10 by advancing sheath 42 over guidewire 28 (and device 10) to a position adjacent filter 16. The step of advancing sheath 42 over guidewire 28 may include disposing filter wire 14 within lumen 52 and guidewire 28 within lumen 54. Advancing sheath 42 toward filter 16 can result in sheath 42 contacting strut 38 and the collapsing of filter 16. Collapsed filter 16 can then be disposed within filter chamber 46 and device 10 together with sheath 42 may be removed from the vasculature.

Sheath 42 may be comprised of a metal, polymer, metal-composite, or essentially any appropriate material including those listed above. In some embodiments, support member 48 may comprise a generally stiff pushing member or wire. According to this and other example embodiments, support member 48 may be comprised of a different material than mid-region 50 and/or distal region 44.

Figure 3:
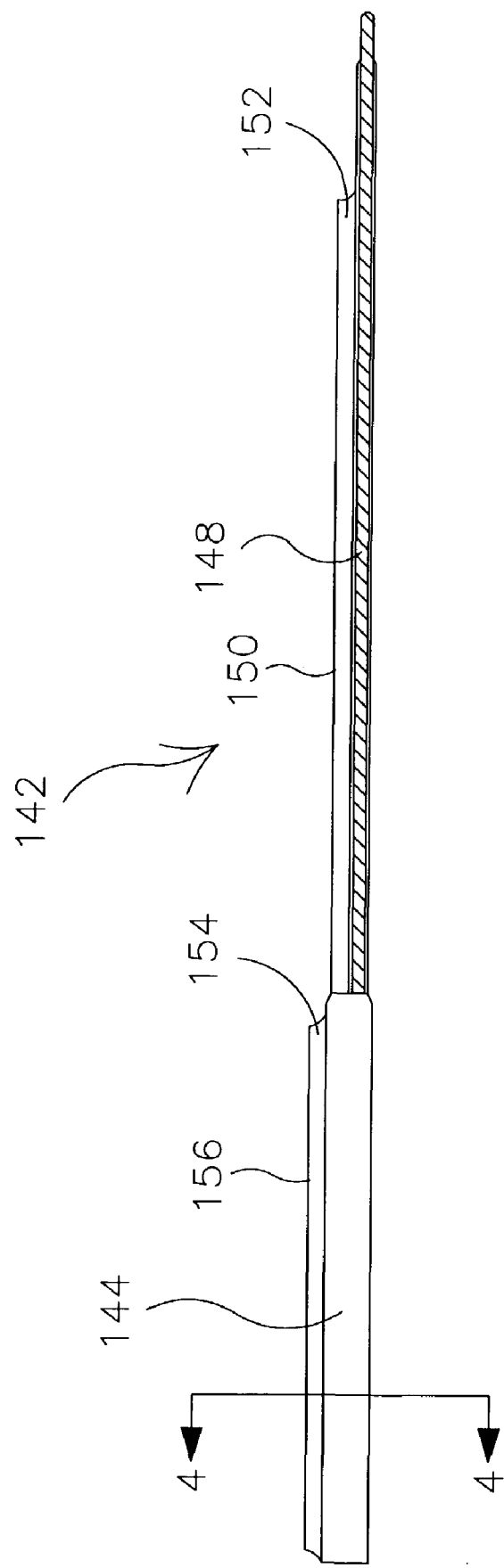
FIG. 3 is a partial cross-sectional side view of another example embolic protection delivery and/or retrieval sheath.

Another example sheath 142 is illustrated in FIG. 3. Sheath 142 is essentially the same in form and function as sheath 42 except that the position of second lumen 154 is altered so as to be generally disposed near the top of distal region 144. In some embodiments, his feature can be accomplished by disposing a tubular rail member 156 (having lumen 154 extending therethrough) adjacent the top of distal region 144. Tubular rail member 156 may be a component of distal region 144 or may be a separate tubular structure attached to distal region 144 by any suitable attachment. The materials used to construct sheath 142 may include any of those listed above or any suitable material.

Sheath 142 also may include support member 148, mid-region 150, and first lumen 152. As it can be seen in FIG. 3, support member 148 may be attached to sheath 142 by disposing or embedding a portion thereof within mid-region 150. Although FIG. 3 illustrates a portion of support member 148 generally being embedded along the length of mid-region 150, it can be appreciated that other embodiments include support member 148 being embedded within only a portion of mid-region 150 or otherwise attached to sheath 142 at any suitable location.

Figure 4:
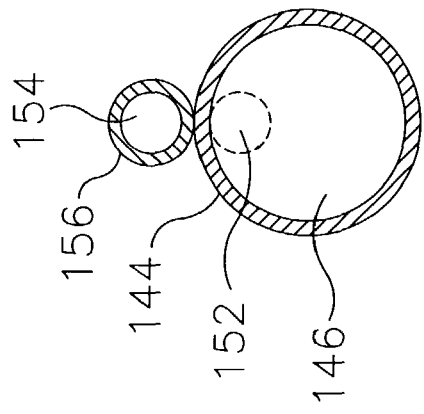
FIG. 4 is a transverse cross-sectional view of an example embolic protection delivery and/or retrieval sheath.

A cross-sectional view of distal region 144 taken through line 4-4 is shown in FIG. 4, which illustrates tubular rail member 156 and distal region 144. As stated above, tubular rail member 156 and distal region 144 may be different structural elements or may comprise a single or composite structure. FIG. 4 also shows the approximate location of lumen 152 in phantom lines and a portion of filter chamber 146.

Figure 5:
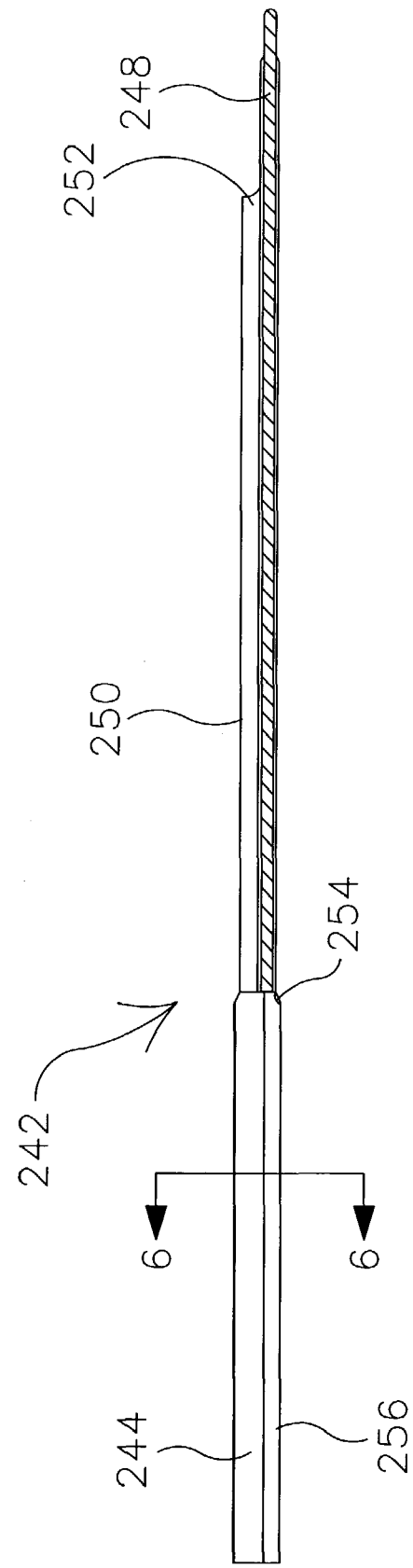
FIG. 5 is a partial cross-sectional side view of another example embolic protection delivery and/or retrieval sheath.

Another example sheath 242 is illustrated in FIG. 5. Sheath 242 is essentially the same in form and function as sheath 142 except that tubular rail member 256 is generally disposed near the bottom of distal region 244. In at least some embodiments, tubular rail member 256 may be partially embedded within distal region 244 (best seen in FIG. 6). Sheath 242 also may include support member 248, mid-region 250, first lumen 252, and second lumen 254. The manufacturing and use of sheath 242 is essentially the same as described above for sheaths 42/142.

Figure 6:
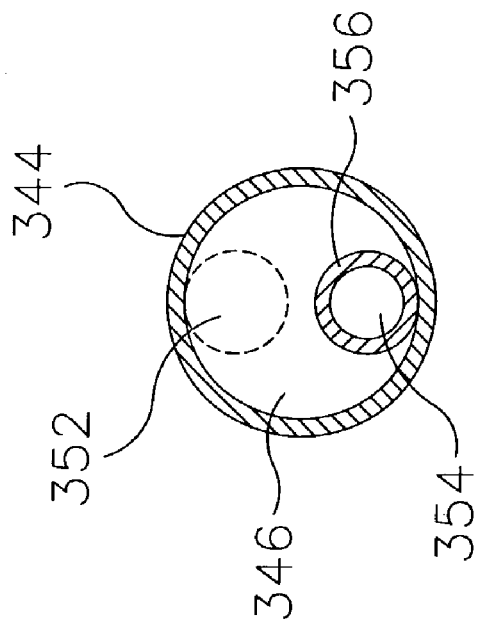
FIG. 6 is a transverse cross-sectional view of an example embolic protection delivery and/or retrieval sheath.

A cross-sectional view of distal region 244, taken through line 6-6 is shown in FIG. 6. From this figure is can be seen that tubular rail member 256 can be embedded within a portion of the wall of distal region 244. Also shown in FIG. 6 is the approximate position of filter chamber 246, first lumen 252 (in phantom), and second lumen 254.

Figure 7:
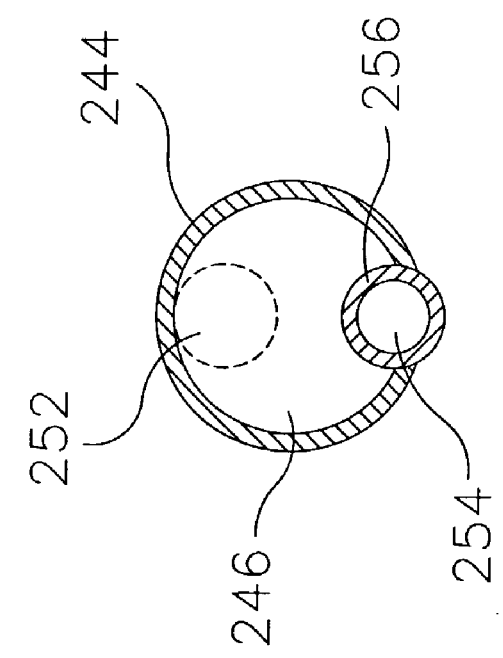
FIG. 7 is a transverse cross-sectional view of an example embolic protection delivery and/or retrieval sheath.

An alternative cross-sectional view taken through line 6-6 is shown in FIG. 7. This figure illustrates an alternative example distal region 344 where tubular rail member 356 may disposed along an inside wall of distal region 344 and within or adjacent filter chamber 346. Similar to what is described above in relation to FIG. 4, tubular rail member 356 may be a distinct structural element disposed on the inside wall of distal region 344 or may be a component of distal region 344. FIG. 7 also shows the approximate location of first lumen 352 (in phantom) and second lumen 354.

Figure 8:
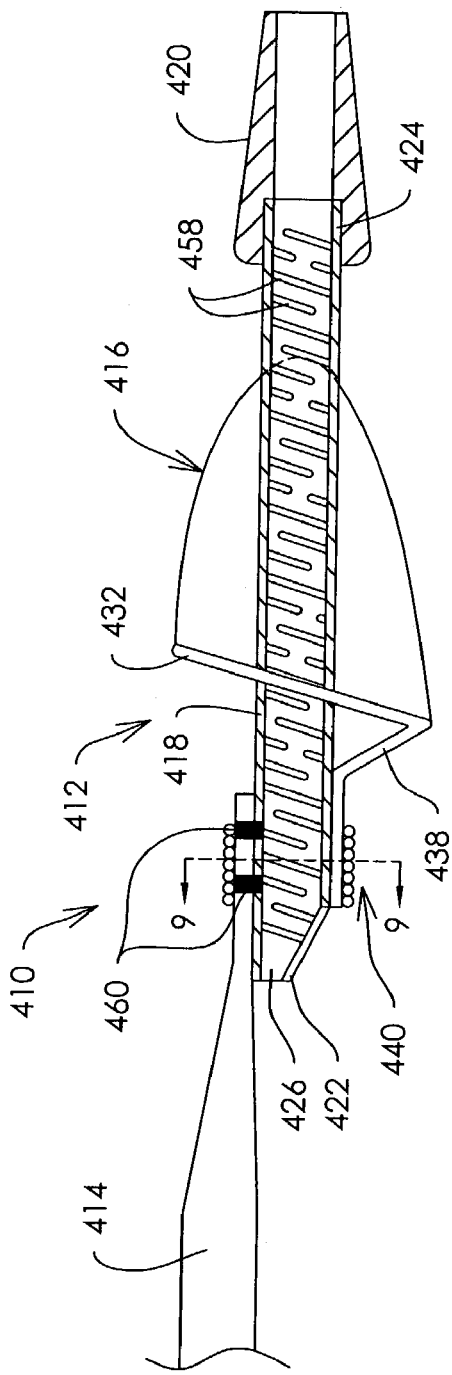
FIG. 8 is a partial cross-sectional side view of another example embolic protection filter system.

FIG. 8 is a partial cross-sectional view of another example filtering device 410. Device 410 may include filter wire assembly 412 including filter wire 414, tubular member 418, and nosecone 420 coupled to tubular member 418. Filter 416 can be coupled adjacent tubular member 418. In at least some embodiments, device 410 can be used in combination with any of the above sheaths and/or any other appropriate delivery and retrieval sheaths and can be essentially the same in form, material composition, and function as device 10. For example, filter 416 may be similar to filter 16 and include frame 432 and one or more (e.g., two) struts 438.

Tubular member 418 may include proximal end 422, distal end 424, and lumen 426 extending therethrough. Similar to what is described above, tubular member 418 may be adapted and configured for having essentially any guidewire or other suitable medical device disposed therein. This feature can allow a user of device 410 to advance it to the desired location over any appropriate medical device.

Tubular member 418 may also include one or more notches or slots 458 disposed along the length thereof. Notches 458 may be configure to alter the flexibility of device 410 adjacent tubular member 418. For example, disposing a number of notches 458 along the length of tubular member 418 may increase the flexibility of tubular member 418. This feature may be desirable, for example, when advancing device 410 through the tortuous vasculature.

Notches 458 may be formed in a number of different ways and may have a number of different configurations. For example, notches 458 may comprise micro-machined openings that are cut into tubular member 418. Alternatively, notches 458 may comprise a spiral cut or groove, a braid, a slot or slots, or the like disposed along the length of tubular member 418. The general dispersal of notches 458 may also be varied. For example, notches 458 may be disposed along essentially the entire length of tubular member 418, a portion of tubular member 418, intermittently or irregularly along tubular member, or any other suitable configuration.

Device 410 may also include shaft or filter wire 414. Filter wire 414 may be fastened to tubular member 418 in a number of appropriate ways including one or more welds 460 (e.g., about 4-10 or more welds 460) and/or coupling 440. Additionally, other bonding mechanisms may be used including adhesive bonding, mechanical bonding, thermal bonding, thermal forming, brazing, thermal-reforming (e.g., I/R heat flow or reflow), heat shrink techniques, and the like, or combinations thereof. In some embodiments, coupling 440 may comprise a coil disposed over filter wire 414, tubular member 418, and struts 438 that may provide structural support at the connection point. Alternatively, coupling 440 may comprise winding of struts 438 about wire 414 and tubular member 418, a marker band or other radiopaque structure, or other suitable structures.

Figure 9:
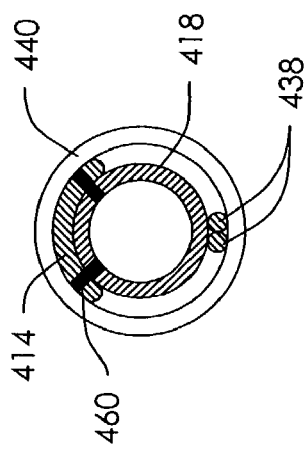
FIG. 9 is a cross-sectional view through line 9-9 of the system shown in FIG. 8.

A cross-sectional view of device 410 taken through line 9-9 is shown in FIG. 9. This figure illustrates tubular member 418 having filter wire 414 coupled thereto, two struts 438, and coupling member 440. It should be noted that the number (two) and the position (adjacent one another) of struts 438 may be varied in alternative embodiments. For example, struts 438 may be arranged on opposite sides of tubular member 418 and/or other numbers (e.g., 1, 3, or more) of struts 438 may be included. Also shown are two welds 460 that may be present to facilitate fastening of filter wire 414 to tubular member 418.

A distal portion of filter wire 414 may be flattened and/or rounded at the point of attachment as seen in FIG. 9. This structural feature may allow, for example, device 410 to have a lower crossing profile by reducing the outer diameter of filter wire 414. This structural feature may also be desirable by increasing the area of contact between filter wire 414 and tubular member 418, thereby allowing for a stronger bond to achieved if desired.

Figure 10:
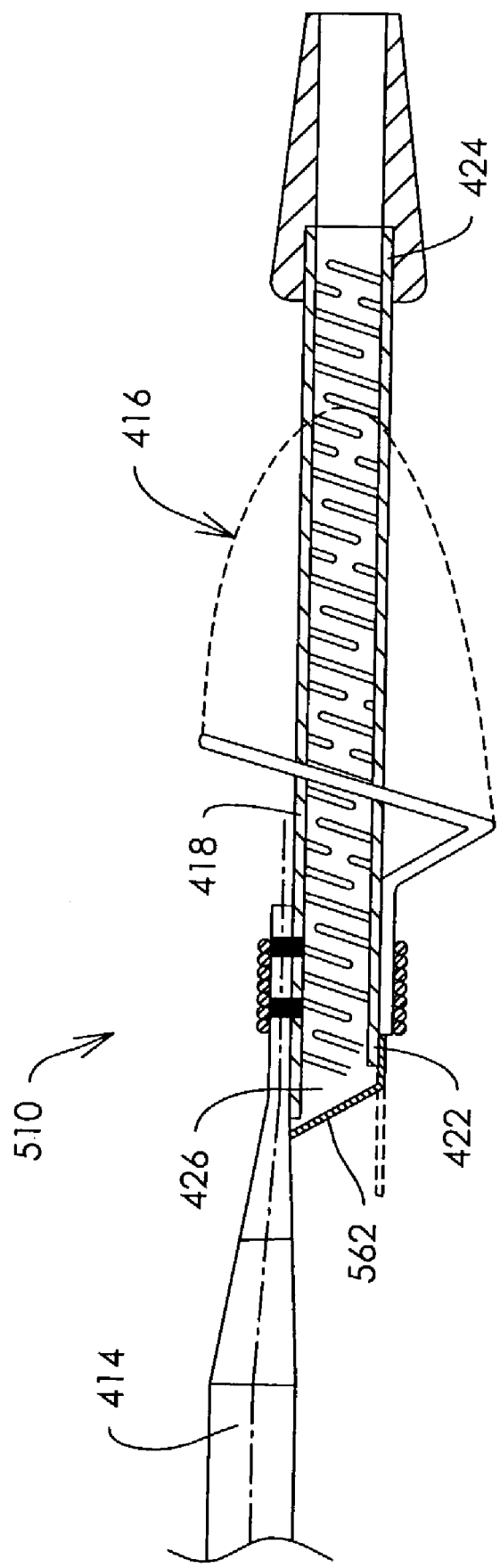
FIG. 10 is a partial cross-sectional side view of an example flow blocking member suitable for use with an embolic protection filtering system.

In some embodiments, it may be desirable to couple restrict the flow of blood or other fluids through lumen 426. An example device 510 is shown in FIG. 10 that is essentially the same in form and function as device 410 except that it includes a flow blocking member 562. Flow blocking member 562 may be coupled adjacent the proximal end of tubular member 418 and can be used to substantially prevent undesired flow of blood or other fluids through tubular member 418. This feature may be desirable, for example, after filter 416 has been delivered to the appropriate target location to prevent blood from essentially "by-passing" filter 416 and flowing through lumen 426.

Flow blocking member 562 may comprise a valve that is adapted and configured to shift between a first generally closed position and a second generally open position. It can be appreciated that when flow blocking member 562 is in the first position, it substantially blocks flow through lumen 426. Shifting to the second position, for example by passing guidewire 28 through lumen 426, substantially opens lumen 426.

In at least some embodiments, flow blocking member 562 can be biased to be in the first position. This feature can be accomplished in a number of different ways including, but not limited to, manufacturing flow blocking member 562 from a linear-elastic or super-elastic alloy shaped to be in the first position but be deflectable toward the second position. Alternatively, the position of flow blocking member 562 can be biased toward the first position by springs or other suitable structures.

Although flow blocking member 562 is shown as being attached adjacent proximal end 422 of tubular member 418, it can be appreciated that flow blocking member 562 can be disposed at essentially any suitable location. For example, disposing flow blocking member 562 adjacent proximal end 422 allows guidewire 28 to be "backloaded" or otherwise pulled back proximally through tubular member 418, thereby shifting member 562 toward the second position. Alternative embodiments may include positioning flow blocking member 562 adjacent distal end 424. This configuration allows guidewire 28 to be advanced distally through tubular member 418, thereby shifting member 562 toward the second position.

FIG. 11 illustrates an example tubular member 618 having an alternative flow blocking member 662 coupled thereto. Tubular member 618 can be essentially the same as any of the other tubular member disclosed herein. Flow blocking member 662 may include a body portion 664 and a number of blockage flaps 666 extending therefrom. Flaps 666 may be configured to shift between a first closed position and a second open position and may be biased to be in the first position similar to what is described above.

Flow blocking member 662 can be described as being a two-way valve due to the fact that flaps 666 can be configured to bend either inward (i.e., toward tubular member 618 as shown in phantom in FIG. 11) or outward. This means that guidewire can pass through flow blocking member 662 in either direction while maintaining the desired flow blocking features.

A spacer or separating ring 668 may be disposed adjacent the junction of flow blocking member 662 and tubular member 618. Spacer 668 can comprise a number of different structures including tubes, solder, other solid or porous structures, and the like. In general, spacer 668 may serve to space at least a region of body portion 664 of flow blocking member 662 from tubular member 618. This may be desirable, for example, by providing additional space for flaps 666 to shift and, therefore, provide space to accommodate objects within tubular member 618.

The shape of flow blocking member 662 and or body portion 664 can vary in differing embodiments. For example, a cross-sectional view of flow blocking member 662 taken through line 12-12 is shown in FIG. 12 that illustrates flow blocking member having a circular end or generally cylindrical shape. Other appropriate shapes may include have a squared shape, a box or parallelepiped shape, or any other shape appropriate for substantially blocking or restricting flow.

FIG. 13 illustrates another example flow blocking member 762 that is similar to member 662 except that it has an expandable hourglass-like shape. More particularly, member 762 may include a first end 770 that can be attached to an example tubular member 718, a mid-region 772, and a second end 774. In general, mid-region 772 can be configured to shift between a first generally closed position and a second generally open position (shown in phantom lines). Mid-region 772 may shift toward the second position when an object like guidewire 28 contacts the inside surface thereof (from either side). This contact begins to enlarge mid-region 772 and, possibly, second end 774, thereby allowing the passing of guidewire 28 therethrough.

Figure 14:
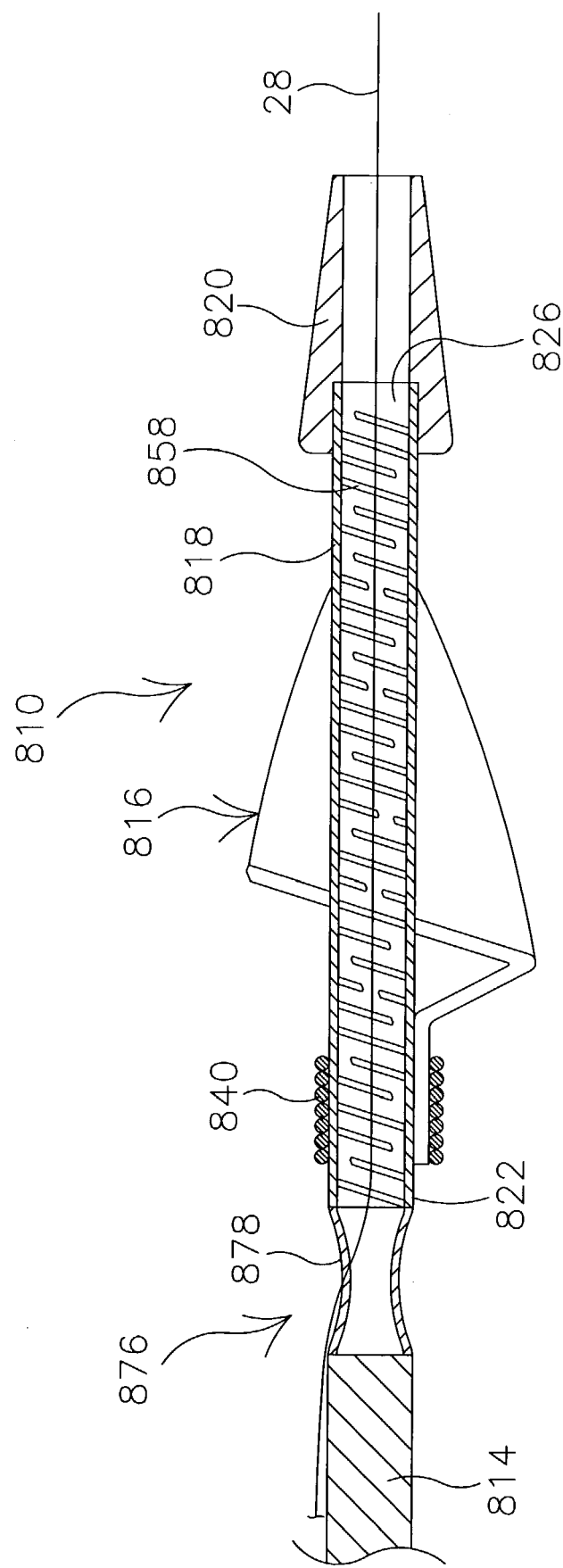
FIG. 14 is a partial cross-sectional side view of another example embolic protection filter system.

Another example filtering device 810 is shown in partial cross-section in FIG. 14. Device 810 is essentially the same in form and function as device 410 except that it includes an intermediate member 876 generally disposed between filter wire 814 and tubular member 818 (e.g., adjacent proximal end 822 thereof). Intermediate member 876 may include one or more openings 878 that are in fluid communication with lumen 826. Thus, device 810 can be advanced over guidewire 28, where guidewire passes through tubular member 818 and through opening 878.

The number of shape, material composition, and length of intermediate member 876 can be varied without altering the scope of the invention. For example, intermediate member 876 may be comprised of any of the materials disclosed herein or any other appropriate material. Moreover, FIG. 14 depicts intermediate member having two openings 878, one near the top and one near the bottom of intermediate member 876. Alternative embodiments include intermediate members 876 having differing numbers of openings 878 (e.g., 1, 3, or more) and differing positions of openings 878.

Intermediate member 876 may be used to smooth or blend the flexibilities of filter wire 814 and tubular member 818. For example, filter wire 814 may comprise a relatively stiff shaft and tubular member 818 may comprise a relatively flexible tube. According to this embodiment, it may be desirable to form a smooth or gentle transition between these flexibilities. Thus, intermediate member 876 may be configured to have a flexibility that blends the flexibility of adjacent structures.

The example embodiment shown in FIG. 14 may desirably reduce the crossing profile of device 810 by axially aligning filter wire 814 and tubular member 818. Thus, the aligned configuration can reduce the number of structures aligned parallel to one another and can reduce the outside diameter of device 810. This structural feature may be desirable when using device 810 in a generally narrow intravascular region or when trying to pass a highly stenosed or occluded vessel.

Figure 15:
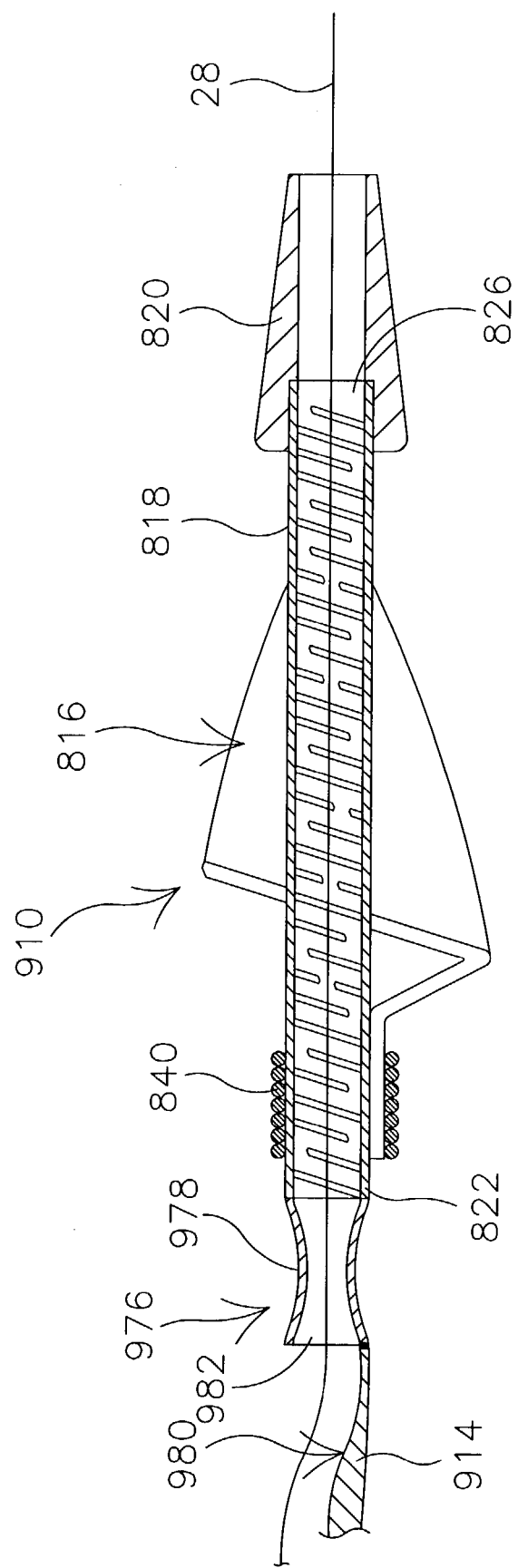
FIG. 15 is a partial cross-sectional side view of another example embolic protection filter system.

Device 810 may also include filter 816, nosecone portion 820, coupling 840, notches 858 within tubular member 818, etc. that include any of the features or alternatives described above for analogous structures. One alternative example embodiment is shown in FIG. 15. FIG. 15 illustrates device 910 that is essentially the same in form and function as device 810 except that filter wire 914 may include a necked region 980 and intermediate member 976 may include both one or more longitudinal openings 978 and an end opening 982, both of which may be in fluid communication with lumen 826.

Necked region 980 of filter wire can provide a smooth transition region for guidewire 28 to enter lumen 826. For example, guidewire 28 can be disposed adjacent necked region 980, pass through opening 982, and pass through lumen 826. This feature may help to reduce friction between guidewire 28 and intermediate member 976 or otherwise reduce the possibility that guidewire 28 might get caught or "hung up" when advancing device 910 over guidewire 28. Necked region 980 can be fastened to intermediate member 976 in any appropriate manner including adhesives, welds, a butt joint, an overlapping joint, etc.

Figure 16:
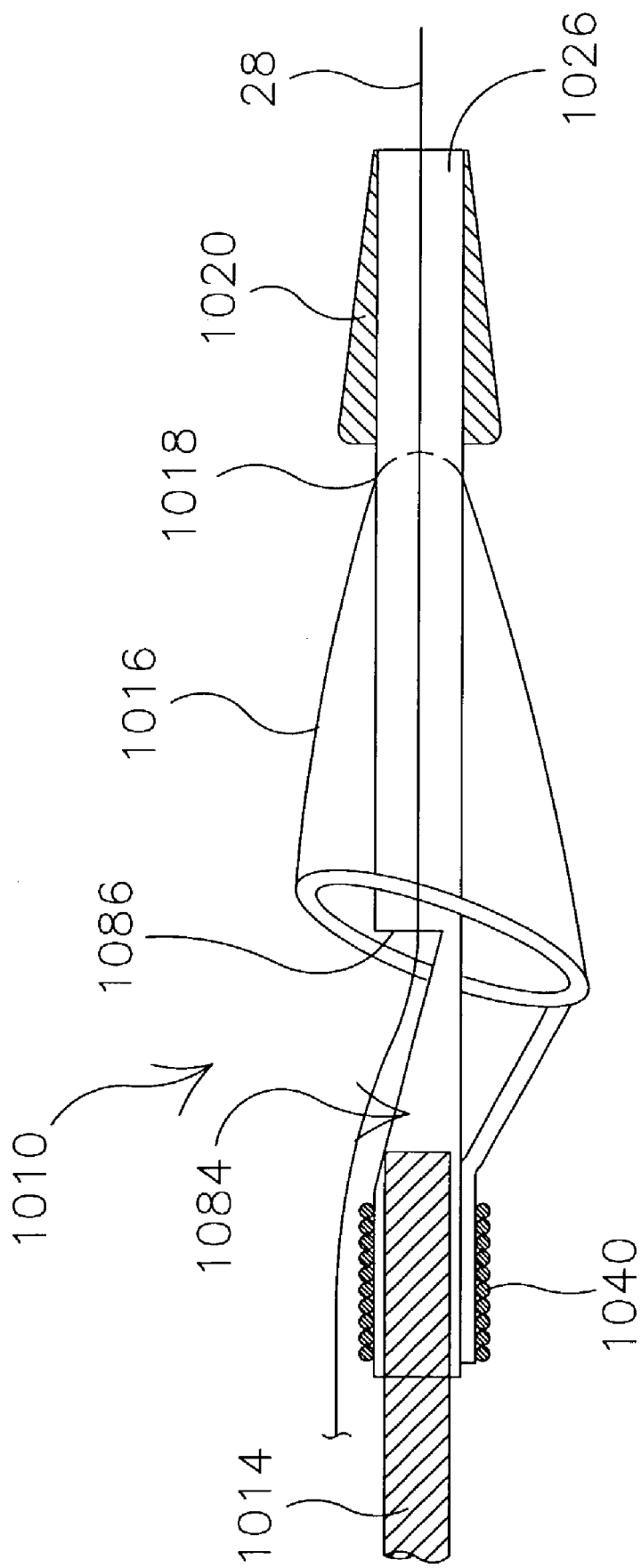
FIG. 16 is a partial cross-sectional side view of another example embolic protection filter system.

Another example filtering device 1010 is shown in FIG. 16. Device 1010 may include filter 1016, nosecone 1020, and filter wire 1014 that can be the same in form and function as those similarly named structures described above. Tubular member 1018 may include a necked region 1084 and an opening 1086 that is in fluid communication with lumen 1026. These features allow guidewire 28 to pass through opening 1086 into lumen 1026 at a different location. Additionally, it can be seen that this embodiment may include coupling 1040 being positioned proximally of opening 1086.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filtering assembly, comprising:
    a guidewire having a distal region;
    a filter wire assembly including an elongate filter wire having a distal end and a tubular member disposed distally adjacent the filter wire distal end, wherein the tubular member has a proximal end, a distal end, and a lumen extending therethrough that can accommodate the guidewire, wherein the distal end of the filter wire is fixedly coupled to the tubular member proximate the proximal end of the tubular member,
    said embolic protection filtering assembly having a first configuration in which the guidewire and the filter wire assembly are separated and a second configuration in which the guidewire is slidably received within the lumen of the tubular member,
    further wherein in the second configuration the tubular member has a first position about the guidewire and removed from the distal region of the guidewire and a second position about the guidewire within the distal region of the guidewire, said tubular member being moveable from the first position to the second position in response to translation of the filter wire parallel to the guidewire; and
    an embolic protection filter coupled to the filter wire assembly, wherein the tubular member extends at least in part through the filter.

2. The embolic protection filtering assembly of claim 1, wherein the lumen is sized to slidably receive a guidewire.

3. The embolic protection filtering assembly of claim 1, wherein the tubular member includes a plurality of notches.

4. The embolic protection filtering assembly of claim 1, wherein the tubular member and the filter wire are arranged substantially parallel to one another.

5. The embolic protection filtering assembly of claim 1, wherein the tubular member and the filter wire are arranged substantially coaxial to one another.

6. The embolic protection filtering assembly of claim 1, wherein the tubular member includes a flow blocking member.

7. The embolic protection filtering assembly of claim 6, wherein the flow blocking member includes one or more blockage flaps.

8. The embolic protection filtering assembly of claim 6, wherein the flow blocking member includes a blockage valve adapted and configure to shift between a first generally open position and a second generally closed position.

9. The embolic protection filtering assembly of claim 1, wherein the filter includes filter frame and one or more struts extending between the filter frame and the filter wire.

10. The embolic protection filtering assembly of claim 9, wherein the struts are coupled to the filter wire by a coupling member.

11. The embolic protection filtering assembly of claim 1, further comprising a sheath having a proximal end, a distal end, a first lumen extending at least partially therethrough, and a second lumen extending at least partially therethrough.

12. The embolic protection filtering assembly of claim 11, wherein the first lumen is defined by a filter wire tube having a tube wall, and wherein the second lumen is defined by a guidewire tube disposed within a least a portion of the tube wall.

13. The embolic protection filtering assembly of claim 11, wherein the first lumen is defined by a filter wire tube having an outer surface, and wherein the second lumen is defined by a guidewire tube disposed on a least a portion of the outer surface.

14. An embolic protection filtering assembly comprising:
a guidewire having a distal region;
an elongate filter wire having a proximal end and a distal end;
a tubular member having a proximal end, the proximal end of the tubular member fixedly coupled to the filter wire adjacent the filter wire distal end, the tubular member having a lumen extending at least partially therethrough that can accommodate the guidewire;
an embolic protection filter coupled to the tubular member, wherein the tubular member extends at least in part through the filter;
said embolic protection filtering assembly having a first configuration in which the guidewire and the tubular member are separated and a second configuration in which the guidewire is slidably received within the lumen of the tubular member,
further wherein in the second configuration the tubular member has a first position about the guidewire and removed from the distal region of the guidewire and a second position about the guidewire within the distal region of the guidewire, said tubular member being moveable from the first position to the second position in response to translation of the filter wire parallel to the guidewire.

15. The embolic protection filtering device of claim 14, wherein the tubular member includes one or more notches.

16. The embolic protection filtering device of claim 14, wherein the tubular member includes a proximal end that is disposed proximally of the filter.

17. The embolic protection filtering device of claim 14, wherein the distal end of the filter wire is flattened.

18. The embolic protection filtering device of claim 14, wherein the distal end of the filter wire is curved.

19. The embolic protection filtering device of claim 14, wherein the filter wire and the tubular member are attached by one or more welds.

20. The embolic protection filtering device of claim 14, wherein the filter wire and the tubular member are attached by a coupling member.

21. The embolic protection filtering device of claim 14, further comprising a flow blocking member coupled to the tubular member.

22. The embolic protection filtering device of claim 14, further comprising an intermediate member disposed between the filter wire and the tubular member, the intermediate member including at least one opening that is in fluid communication with the lumen.

23. The embolic protection filtering device of claim 22, wherein the filter wire includes a necked portion adjacent the intermediate tube.

24. The embolic protection filtering device of claim 14, wherein the tubular member includes a necked region and an opening adjacent the necked region, the opening being in fluid communication with the lumen.

25. An embolic protection filtering assembly comprising:
a guidewire having a distal region;
a tubular member having a length, a proximal end, a distal end, and a lumen extending therethrough that can accommodate the guidewire;
the tubular member having one or more notches disposed along the length thereof; a nosecone coupled to the tubular member adjacent the distal end;
wherein the lumen is sized for advancing the tubular member over an elongate medical device;
an embolic protection filter coupled to the tubular member, the filter including a filter frame, a filtering material coupled to the filter frame, and one or more struts extending between the filter frame and the tubular member, wherein the tubular member extends at least in part through the filter; and
an elongate filter wire having a distal end, said distal end fixedly coupled to the tubular member adjacent the proximal end of the tubular member,
said embolic protection filtering assembly having a first configuration in which the guidewire and the tubular member are separated and a second configuration in which the guidewire is slidably received within the lumen of the tubular member,
further wherein in the second configuration the tubular member has a first position about the guidewire and removed from the distal region of the guidewire and a second position about the guidewire within the distal region of the guidewire, said tubular member being moveable from the first position to the second position in response to translation of the filter wire parallel to the guidewire.

26. The embolic protection filtering device of claim 25, wherein the filter wire includes a flattened distal end.

27. The embolic protection filtering device of claim 26, wherein the flattened distal end is curved.

28. The embolic protection filtering device of claim 25, wherein the filter wire and the tubular member are attached by one or more welds.

29. The embolic protection filtering device of claim 25, wherein the filter wire and the tubular member are attached by a coupling member.

30. The embolic protection filtering device of claim 25, further comprising a flow blocking member coupled to the tubular member.

31. The embolic protection filtering device of claim 25, further comprising an intermediate member disposed between the filter wire and the tubular member, the intermediate member including at least one opening that is in fluid communication with the lumen.

32. The embolic protection filtering device of claim 31, wherein the filter wire includes a necked portion adjacent the intermediate tube.

33. The embolic protection filtering device of claim 25, wherein the tubular member includes a necked region and an opening adjacent the necked region, the opening being in fluid communication with the lumen.

34. The embolic protection filtering device of claim 25, further comprising a delivery and/or retrieval sheath, the sheath including a filter chamber, a filter wire lumen, and a guidewire lumen.

35. The embolic protection filtering device of claim 34, wherein the guidewire lumen is defined by a rail tube disposed along an outer surface of the filter chamber.

36. The embolic protection filtering device of claim 34, wherein the guidewire lumen is defined by a rail tube disposed along an inner surface of the filter chamber.

37. The embolic protection filtering device of claim 34, wherein the guidewire lumen is defined by a rail tube that is at least partially embedded in the outer wall.

38. The embolic protection filtering device of claim 34, wherein the sheath further comprises a proximal support member.

* * * * *